United States Patent
Kerschner et al.

(10) Patent No.: US 9,655,837 B2
(45) Date of Patent: May 23, 2017

(54) OIL-CONTINUOUS LIQUID CRYSTALLINE PHASE FORMULATION AND USE OF THE SAME

(71) Applicant: INTERNATIONAL FLAVORS & FRAGRANCES, INC., New York, NY (US)

(72) Inventors: Judith Kerschner, Hawthorne, NJ (US); Timothy Young, Middletown, NJ (US); Samantha Bernal, Jersey City, NJ (US); Dennis Muniz, Clark, NJ (US)

(73) Assignee: INTERNATIONAL FLAVORS & FRAGRANCES INC., New York, NY (US)

( * ) Notice: Subject to any disclaimer, the term of this patent is extended or adjusted under 35 U.S.C. 154(b) by 0 days.

(21) Appl. No.: 14/647,737

(22) PCT Filed: Nov. 25, 2013

(86) PCT No.: PCT/US2013/071580
§ 371 (c)(1),
(2) Date: May 27, 2015

(87) PCT Pub. No.: WO2014/085287
PCT Pub. Date: Jun. 5, 2014

(65) Prior Publication Data
US 2015/0306020 A1    Oct. 29, 2015

Related U.S. Application Data

(60) Provisional application No. 61/730,260, filed on Nov. 27, 2012.

(51) Int. Cl.
*C11D 1/65* (2006.01)
*A61K 8/92* (2006.01)
(Continued)

(52) U.S. Cl.
CPC ............. *A61K 8/92* (2013.01); *A61K 8/0295* (2013.01); *A61K 8/39* (2013.01); *A61K 8/416* (2013.01);
(Continued)

(58) Field of Classification Search
CPC .................................. C11D 1/65; C11B 9/00
See application file for complete search history.

(56) References Cited

U.S. PATENT DOCUMENTS 5,523,013 A * 6/1996 Durbut .................. C09K 19/00
510/235
5,599,555 A   2/1997 El-Nokaly
(Continued)

FOREIGN PATENT DOCUMENTS

CN   1658824 A   8/2005
EP   0418986 A2  3/1991
EP   0466235 A1  1/1992

OTHER PUBLICATIONS

Extended European Search Report for European Application No. 13858477.6 mailed on Sep. 23, 2015.
(Continued)

*Primary Examiner* — John Hardee
(74) *Attorney, Agent, or Firm* — Martin Zhang; XuFan Tseng; Elizabeth M. Stover

(57) ABSTRACT

The present invention is an oil-continuous liquid crystalline phase formulation composed of a cationic and anionic surfactant in combination with a fragrance oil as well as a consumer product base containing the same.

3 Claims, 3 Drawing Sheets

(51) Int. Cl.
- *A61Q 5/02* (2006.01)
- *A61K 8/39* (2006.01)
- *A61K 8/41* (2006.01)
- *A61K 8/46* (2006.01)
- *A61Q 13/00* (2006.01)
- *A61Q 19/10* (2006.01)
- *A61K 8/02* (2006.01)
- *C11B 9/00* (2006.01)
- *A61Q 15/00* (2006.01)

(52) U.S. Cl.
CPC ............... *A61K 8/46* (2013.01); *A61K 8/463* (2013.01); *A61K 8/466* (2013.01); *A61Q 5/02* (2013.01); *A61Q 13/00* (2013.01); *A61Q 15/00* (2013.01); *A61Q 19/10* (2013.01); *C11B 9/00* (2013.01); *A61K 2800/56* (2013.01); *A61K 2800/596* (2013.01)

(56) References Cited

U.S. PATENT DOCUMENTS

| | | |
|---|---|---|
| 2006/0154850 A1 | 7/2006 | Ouellet et al. |
| 2006/0165739 A1* | 7/2006 | Komesvarakul ....... A61K 8/068 424/401 |
| 2007/0105746 A1* | 5/2007 | Dahms ................. A61K 8/0295 512/2 |
| 2008/0031845 A1 | 2/2008 | Stella et al. |
| 2008/0057016 A1 | 3/2008 | Geary et al. |
| 2008/0146478 A1 | 6/2008 | Lei et al. |
| 2009/0035365 A1 | 2/2009 | Popplewell et al. |
| 2011/0269657 A1 | 11/2011 | Dihora et al. |
| 2011/0308556 A1 | 12/2011 | Smets et al. |
| 2012/0097754 A1 | 4/2012 | Vlad et al. |
| 2012/0183591 A1 | 7/2012 | Dahms |

OTHER PUBLICATIONS

First Office Action Report for Chinese Application 201380071382.0 mailed on Oct. 14, 2016.

"Lyotropic", Oct. 7, 2015, Retrieved from the Internet: URL:https://en.wikipedia.org/wiki/Lyotropic [retrieved on Apr. 4, 2016].

Supplementary European Search Report for Application No. 13858666.4 mailed on Jul. 18, 2016.

Second Office Action Report for Chinese Application No. 201380071382.0 mailed on Feb. 6, 2017.

Office Action for U.S. Appl. No. 14/647,754 mailed on Oct. 16, 2015.

* cited by examiner

OIL-CONTINUOUS LIQUID CRYSTALLINE PHASE FORMULATION AND USE OF THE SAME

CROSS REFERENCE TO RELATED APPLICATIONS

This application is the national stage entry under 35 USC 371 for PCT/US2013/071580, filed on Nov. 25, 2013, which claims the benefit of U.S. Provisional Application No. 61/730,260 filed on Nov. 27, 2012. The contents of the foregoing applications are incorporated herein by reference.

BACKGROUND OF THE INVENTION

A difficulty encountered with fragranced personal cleansing compositions is that the fragrance oils are solubilized within the surfactant micelles such that they either remain micellized or enter the continuous aqueous phase. Either way, the result is that they are typically rinsed away during the washing process rather than being deposited onto the skin as intended.

Previous work has employed a number of methods to counter this effect. One approach discussed in EP 0554024 has been to reduce solubilization of the perfume oil in the surfactant phase by adding an oil phase in which the perfume oils may reside. As a result of the oil's natural hydrophobicity, that oil phase, including the perfume oil, may deposit relatively well onto skin. A similar approach is discussed in WO 03/015736, which relates to the dissolution of the perfumes in a water-immiscible silicone phase. Again, the naturally hydrophobic silicone phase may lead to improved deposition of the fragrance oil onto skin. These approaches involve the inclusion of an additional material to the formulation to enhance fragrance delivery. That additional material may, however, have negative implications for the overall performance of the formulation, such as the lather profile.

An alternative approach discussed in WO 97/48374, WO 97/48375 and WO 97/48378, has been to form coacervates between anionic surfactant and cationic polymers, which coacervates are allegedly capable of entrapping the perfume, depositing on the skin and thus enhancing perfume deposition.

A further alternative discussed in US 2003/166497, US 2003/166498 and US 2003/166499 has been to design the perfume/surfactant system such that, on dilution, micelles are designed to disappear due to their high Critical Micelle Concentration (CMC), and deliver fragrance bloom. After blooming from the micelles, the perfume materials enter the water continuous phase and may be washed away during rinsing. Once again, the surfactant phase is essentially a micellar phase.

Additional approaches employing various surfactants are described in GB 1440975, EP 117135, EP 23676, U.S. Pat. No. 5,035,826, U.S. Pat. No. 5,661,189, US 2009/0312223, and EP 0347199.

SUMMARY OF THE INVENTION

This invention is an oil-continuous liquid crystalline phase formulation composed of dioleoyl ammonium methosulfate, sodium tridecyl sulphosuccinate, and a fragrance oil, e.g., in a ratio of about 5:3:7. This invention is also an oil-continuous liquid crystalline phase formulation composed of sodium dioctyl sulfosuccinate, a fragrance oil and a cationic surfactant, e.g., methyl bis(hydrogenated tallow amidoethyl)-2-hydroxyethyl ammonium methyl sulfate, methyl bis(tallow amidoethyl)-2-hydroxyethyl ammonium methyl sulfate, methyl bis(soya amidoethyl)-2-hydroxyethyl ammonium methyl sulfate, methyl bis(canola amidoethyl)-2-hydroxyethyl ammonium methyl sulfate, methyl bis(tallowamido ethyl)-2-tallow imidazolinium methyl sulfate, dioleoyl ammonium methosulfate or dipalmityl ammonium methosulfate. Consumer products containing the oil-continuous liquid crystalline phase formulations of this invention are also provided.

DETAILED DESCRIPTION OF THE INVENTION

It has now been found that the deposition of perfume onto skin, hair and/or fabric can be enhanced by manipulating surfactant phase behavior. In particular, this invention is an oil-continuous liquid crystalline phase formulation for binding aroma compounds and use of the same in consumer products. The oil-continuous phase is composed of a particular combination of surfactants, which form the liquid crystalline phase and contains a very high concentration of both fragrance oil (e.g., aldehydes and alcohols, and possibly some esters and ketones and lactones of high polarity) and surfactant. The phase thus formed, when re-dispersed into consumer product bases such as fabric softeners, shower gels, shampoos or liquid detergents, will retain high levels of fragrance that are not completely dissolved or solubilized in the consumer product base. When the product is used, in a wash, rinse application, the surface active fragrance compounds that are tied up in the liquid crystal or semi-solid phase may remain un-dissolved fully or may dissolve late in the wash or rinse product thereby imparting higher levels on skin, fabric, hair, etc.

Figure 1:
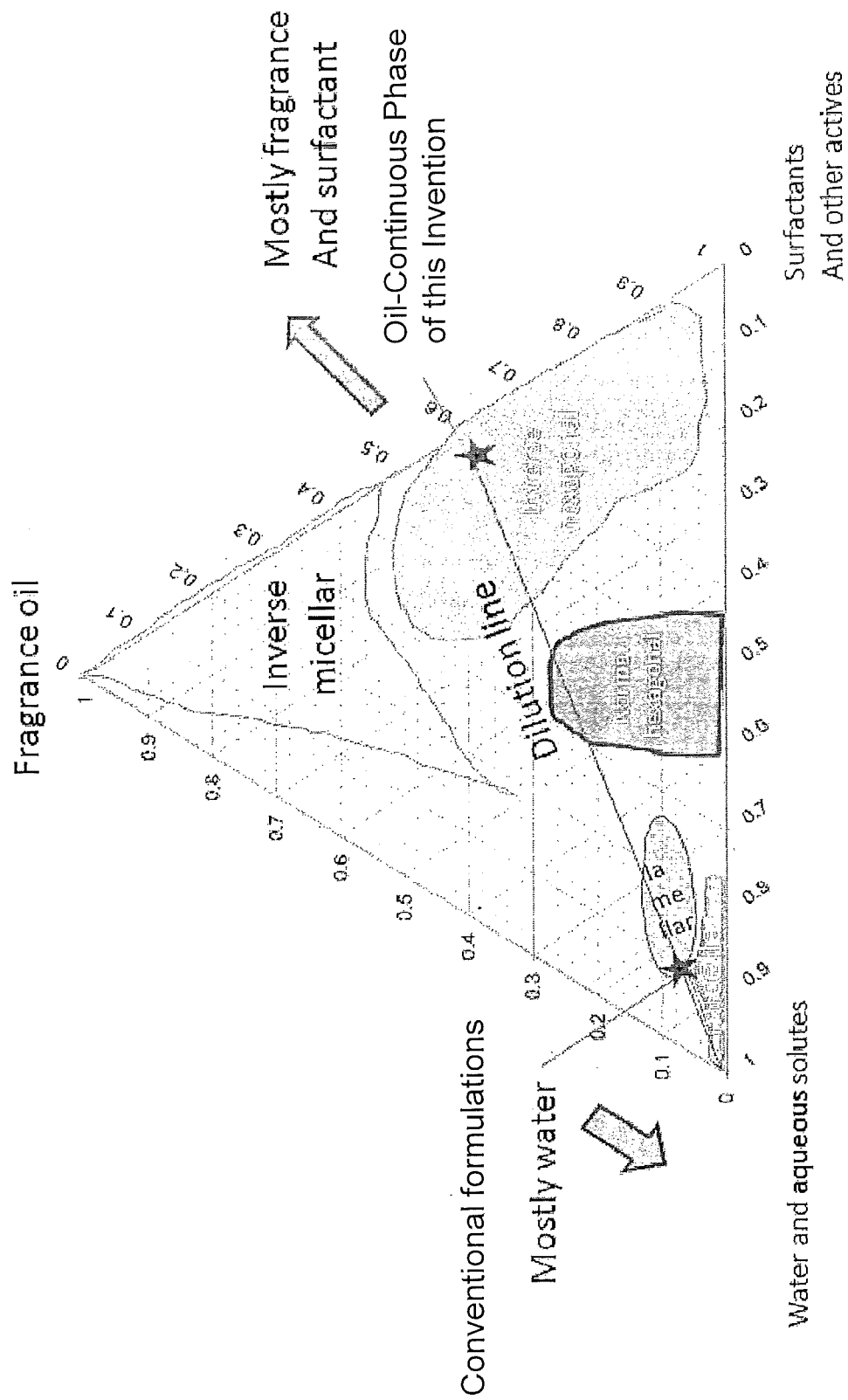
FIG. 1 shows a phase diagram of the formulation of the invention.

The liquid crystalline formulation of this invention is a structured surfactant composition having an ordered liquid crystal structure. In accordance with the formulation of this invention, very high levels of fragrance are combined with low Hydrophilic-lipophilic balance (HLB), water insoluble surfactants to obtain a phase which is oil-continuous or bicontinuous rather than water continuous, wherein the phases do not extend from the micellar phase (FIG. 1). The phases of this invention extend from the "inverse micellar" (water cores in oil media, rather than the reverse). Some do and some do not rotate plane polarized light. Using the present formulations, two or more additional phases to the micellar phase can occur. The continuous phase can be determined experimentally by testing the conductivity with a conductivity meter or using an impedance analyzer.

In general, the formulation of the invention includes one or more cationic surfactant(s), one or more anionic surfactant(s) and a fragrance oil. In certain embodiments, the formulation of the invention does not include a silicone, e.g., an arylated silicone.

The oil-continuous phase according to the invention may include from about 10% wt to about 50% wt surfactant, preferably from about 20% wt to about 40% wt, or more preferably from about 30% wt.

Anionic surfactants which may be used in this invention include alkyl sulfates, alkyl ether sulfates, sulfated monoglycerides, sulfonated olefins, alkyl aryl sulfonates, primary or secondary alkane sulfonates, alkyl sulfosuccinates, acyl taurates, acyl isethionates, alkyl glycerylether sulfonate, sulfonated methyl esters, sulfonated fatty acids, alkyl phosphates, acyl glutamates, acyl sarcosinates, alkyl sulfoacetates, acylated peptides, alkyl ether carboxylates, acyl lactylates, and combinations thereof. In some embodiments, the anionic surfactant is a sulfosuccinate or sulfate. Sulfosuccinates include, but are not limited to the dialkylsulfosuccinates such as sodium dioctylsulfosuccinate, sodium ditridecylsulfosuccinate, sodium didecylsulfosuccinate, sodium tridecyl sulfosuccinate, or blends thereof. In particular embodiments, the anionic surfactant is sodium tridecyl sulfosuccinate or sodium dioctyl sulfosuccinate. Sulphonates of use in this invention, include, but are not limited to sodium benzene alkyl sulphonate.

The formulation according to the invention may include from about 1% wt to about 70% wt anionic surfactant, preferably from about 1% wt to about 60% wt, more preferably from about 10% wt to about 50% wt, even more preferably from about 10% wt to about 45% wt, more preferably still from about 15% to about 50% wt.

Cationic surfactants which may be employed according to the invention include, e.g., fatty amines, di-fatty quaternary amines, trifatty quaternary amines, imidazolinium quaternary amines, and combinations thereof. Suitable cationic surfactants are particularly cetyl trimethyl ammonium chloride, palmitamidopropyltrimonum chloride, dipalmitoyltrimonium chloride, distearyldimonium chloride, dipalmitoylethylhydroxyethylmonium chloride, dioleoylethyl ammonium methosulfate, dioleoylethyl hydroxyethylmonium methosulfate, dilinolamidopropyldimonium chloride, dioleylethyl hydroxyethylmonium chloride, dipalmitoylethyldimonium chloride and or didodecyl dimethyl ammonium chloride. In particular embodiments, the cationic surfactant is dioleoyl ammonium methosulfate. In other embodiments, the cationic surfactant is methyl bis(hydrogenated tallow amidoethyl)-2-hydroxyethyl ammonium methyl sulfate, methyl bis(tallow amidoethyl)-2-hydroxyethyl ammonium methyl sulfate, methyl bis(soya amidoethyl)-2-hydroxyethyl ammonium methyl sulfate, methyl bis(canola amidoethyl)-2-hydroxyethyl ammonium methyl sulfate, methyl bis(tallowamido ethyl)-2-tallow imidazolinium methyl sulfate, dioleoyl ammonium methosulfate, or didodecyl dimethyl ammonium chloride, dipalmityl ammonium methosulfate, or blends thereof.

The formulation according to the invention may include from about 1% wt to about 30% wt cationic surfactant, preferably from about 5% wt to about 30% wt, more preferably from about 10% wt to about 25% wt, even more preferably from about 12% wt to about 25% wt.

As mentioned, the surfactant of the formulation of this invention advantageously includes both anionic and cationic surfactants. With anionic-cationic binary surfactant systems, oil continuous phases occur upon addition of water and oil. These depend strongly on surfactant ratio, which are experimentally determined. However, total surfactant and oil ratios are the same as for single surfactant systems. See Example 3.

A formulation according to the invention includes a fragrance oil. As referred to herein, the term "fragrance oil" refers to perfume materials and may include single perfume raw materials or blends of oils. A wide variety of chemicals may be employed as or included in the fragrance oil, including materials such as aldehydes and alcohols, as well as some esters and ketones and lactones of high polarity. More commonly, naturally occurring plant and animal oils and exudates including complex mixtures of various chemical components are known for use as or inclusion in Fragrance Oils.

Examples of fragrance oils useful herein include, but are not limited to, animal fragrances such as musk oil, civet, castoreum, ambergris, plant fragrances such as nutmeg extract, cardamom extract, ginger extract, cinnamon extract, patchouli oil, geranium oil, orange oil, mandarin oil, orange flower extract, cedarwood, vetyver, lavandin, ylang extract, tuberose extract, sandalwood oil, bergamot oil, rosemary oil, spearmint oil, peppermint oil, lemon oil, lavender oil, citronella oil, chamomile oil, clove oil, sage oil, neroli oil, labdanum oil, eucalyptus oil, verbena oil, mimosa extract, narcissus extract, carrot seed extract, jasmine extract, olibanum extract, rose extract and mixtures thereof.

Other examples of suitable fragrance oils include, but are not limited to, chemical substances such as acetophenone, adoxal, aldehyde C-12, aldehyde C-14, aldehyde C-18, allyl caprylate, ambroxan, amyl acetate, dimethylindane derivatives, $\alpha$-amylcinnamic aldehyde, anethole, anisaldehyde, benzaldehyde, benzyl acetate, benzyl alcohol and ester derivatives, benzyl propionate, benzyl salicylate, borneol, butyl acetate, camphor, carbitol, cinnamaldehyde, cinnamyl acetate, cinnamyl alcohol, cis-3-hexenol and ester derivatives, cis-3-hexenyl methyl carbonate, citral, citronellol and ester derivatives, cumin aldehyde, cyclamen aldehyde, cyclo galbanate, damascones, decalactone, decanol, estragole, dihydromyrcenol, dimethyl benzyl carbinol, 6,8-dimethyl-2-nonanol, dimethyl benzyl carbinyl butyrate, ethyl acetate, ethyl isobutyrate, ethyl butyrate, ethyl propionate, ethyl caprylate, ethyl cinnamate, ethyl hexanoate, ethyl valerate, ethyl vanillin, eugenol, exaltolide, fenchone, fruity esters such as ethyl 2-methyl butyrate, galaxolide, geraniol and ester derivatives, helional, 2-heptonone, hexenol, $\alpha$-hexylcinnamic aldehyde, hydroxycitronellal, indole, isoamyl acetate, isoeugenol acetate, ionones, isoeugenol, isoamyl iso-valerate, iso E super, limonene, linalool, lilial, linalyl acetate, lyral, majantol, mayol, melonal, menthol, p-methylacetophenone, methyl anthranilate, methyl cedrylone, methyl dihydrojasmonate, methyl eugenol, methyl ionone, methyl-$\beta$-naphthyl ketone, methylphenylcarbinyl acetate, mugetanol, $\gamma$-nonalactone, octanal, phenyl ethyl acetate, phenyl-acetaldehyde dimethyl acetate, phenoxyethyl isobutyrate, phenyl ethyl alcohol, pinenes, sandalore, santalol, stemone, thymol, terpenes, triplal, triethyl citrate, 3,3,5-trimethylcyclohexanol, $\gamma$-undecalactone, undecenal, vanillin, veloutone, verdox and mixtures thereof.

Suitable fragrance oils can be found in U.S. Pat. Nos. 4,145,184, 4,209,417, 4,515,705, and 4,152,272, all of which are incorporated herein by reference.

The formulation according to the invention may include from about 15% wt to about 60% wt fragrance oil, preferably from about 20% wt to about 50% wt, more preferably from about 25% wt to about 40% wt, even more preferably from about 30% wt to about 35% wt, more preferably still about 35% wt.

The ratio of surfactant to fragrance oil is from about 3:1 to about 1:1, more preferably about 8:7. In some embodiments, the ratio of surfactant to fragrance oil is about 3:1. In other embodiments, the ratio of surfactant to fragrance oil is about 2:1. In still other embodiments, the ratio of surfactant to fragrance oil is about 1:1. In certain embodiments, the ratio of cationic surfactant:anionic surfactant:fragrance oil is about 5:3:7; 7:43:50; 12:37:50; or 9:66:25.

In certain embodiments, the formulation of this invention also includes an aqueous component such as water. Typically, the aqueous component is from about 0% wt to about 30% wt of the formulation, preferably from about 10% wt to about 30% wt, more preferably from about 15% wt to about 30% wt, even more preferably from about 20% wt to about 25% wt.

An exemplary formulation of this invention is an oil-continuous liquid crystalline phase formulation comprising dioleoyl ammonium methosulfate, sodium tridecyl sulphosuccinate, and a fragrance oil. In particular, an oil-continuous liquid crystalline phase formulation of this invention comprises or consists of dioleoyl ammonium methosulfate, sodium tridecyl sulphosuccinate, a fragrance oil and water. In accordance with this particular embodiment, the ratio of cationic surfactant:anionic surfactant:fragrance oil:water is about 5:3:7:5.

Other exemplary formulations of this invention are oil-continuous liquid crystalline phase formulations comprising sodium dioctylsulfo-succinate, a fragrance oil, and methyl bis (Soya amidoethyl) hydroxyethlyl ammonium methyl sulfate or dipalmityl ammonium methosulfate. In particular, an oil-continuous liquid crystalline phase formulation of this invention comprises or consists of sodium dioctylsulfo-succinate, a fragrance oil, and methyl bis (Soya amidoethyl) hydroxyethlyl ammonium methyl sulfate or sodium dioctyl-sulfo-succinate, a fragrance oil, and dipalmityl ammonium methosulfate.

Advantageously, the surfactants of the invention are soluble in the fragrance oil, and therefore richer in fragrance and surfactant, with much less water than conventional formulations. The present invention does not require the higher overall use level of fragrance in a consumer product (e.g., 2-4%), and can achieve 1% fragrance or less overall, as the fragrance is already in the surfactant phase. For example, when the formulation of the invention is prepared and forms the oil-continuous liquid crystalline phase, it possesses kinetic stability when added to a base, at a level of 3-4 weight %, to produce an overall fragrance concentration of 1% in a finished product.

When the crystalline phase structure is re-dispersed into surfactant containing bases, like fabric softener, shower gels, shampoos and liquid detergents, it is contemplated that the formulation will retain the structure with high levels of fragrance that is not completely dissolved or solubilized in the product base. When the product is used, in a wash, rinse application, the surface active fragrance compounds that are tied up in the liquid crystal or semi-solid phase are expected to remain un-dissolved fully or may dissolve late in the wash or rinse product. This effect causes the fragrance oils to occur at higher levels on skin, fabric, hair, etc. following a wash or rinse procedure thereby allowing for possible higher deposition and substantivity of certain aroma notes that a consumer may notice and appreciate.

Accordingly, the oil-continuous liquid crystalline phase formulation of this invention finds particular use in the consumer product bases, e.g., fabric care products, including detergents, fabric conditioners, and the like; as well as personal care products which include shampoos, body wash, conditioners, hair rinses, hair refreshers, body washes, soaps, anti-perspirants, deodorants and the like. These products are well known in the art. For example, fabric softener systems are described in U.S. Pat. Nos. 6,335,315, 5,674,832, 5,759,990, 5,877,145, 5,574,179; 5,562,849, 5,545,350, 5,545,340, 5,411,671, 5,403,499, 5,288,417, 4,767,547, 4,424,134. Shampoo and conditioners that can employ the present invention include U.S. Pat. Nos. 6,162,423, 5,968,286, 5,935,561, 5,932,203, 5,837,661, 5,776,443, 5,756,436, 5,661,118, 5,618,523, 5,275,755, 5,085,857, 4,673,568, 4,387,090 and 4,705,681.

In certain embodiments, the final consumer product or composition may be in the form of an oil, a gel, a solid stick, a lotion, a cream, a milk, an aerosol, a spray, a powder, a foam, a shampoo, a hair conditioner, a lacquer or a make-up.

Consumer product compositions according to the invention may also comprise vitamins and derivatives thereof, sunscreens, preservatives, chelators and sequestrants and aesthetic agents such as dyes, mica, titanium dioxide, ethylene glycol distearate (EGDS).

Example 1: Cubic Liquid Crystalline Phase

Oil-continuous liquid crystalline phase formulations (#1 and #2), which form cubic liquid crystalline phases, were prepared (Table 1).

TABLE 1

| Form. | Surfactant 1 | Surfactant 2 | Fragrance Oil (%) | Water (%) |
|---|---|---|---|---|
| #1* | 15% sodium benzene alkyl sulphonate | 35% tetra ethoxy nonyl phenol | 25% | 25% |
| #2 | 25% Dioleoyl ammonium methosulfate | 15% Sodium tridecyl sulphosuccinate | 35% | 25% |

*This formulation is particularly suited for a shower gel or shampoo base.

Example 2: Inverse Hexagonal Phase

Oil-continuous liquid crystalline phase formulations (#3, #4, #5, and #6), which form an inverse hexagonal phase, were prepared (Table 2) and introduced into a shampoo base.

TABLE 2

| Form. | Surfactant 1 | Surfactant 2 | Fragrance Oil (%) |
|---|---|---|---|
| #3 | 43% Sodium dioctylsulfo-succinate | 7% methyl bis(Soya amidoethyl) hydroxyethlyl ammonium methyl sulfate | 50% |
| #4 | 37.5% sodium dioctyl sulfosuccinate | 12.5% methyl bis(Soya amidoethyl) hydroxyethlyl ammonium methyl sulfate | 50% |
| #5 | 37.5% sodium dioctyl sulfosuccinate | 12.5% Dipalmityl Ammonium Methosulfate | 50% |
| #6 | 66% sodium dioctyl sulfosuccinate | 9% methyl bis(Soya amidoethyl) hydroxyethlyl ammonium methyl sulfate | 25% |
| #7 | 45% sodium bis-tridecyl sulfosuccinate | 24% didodecyl dimethyl ammonium chloride | 31% |
| #8 | 63% sodium bis-tridecyl sulfosuccinate | 6% didodecyl dimethyl ammonium chloride | 31% |
| #9 | 17% sodium bis-tridecyl sulfosuccinate | 52% didodecyl dimethyl ammonium chloride | 31% |

Figure 2:
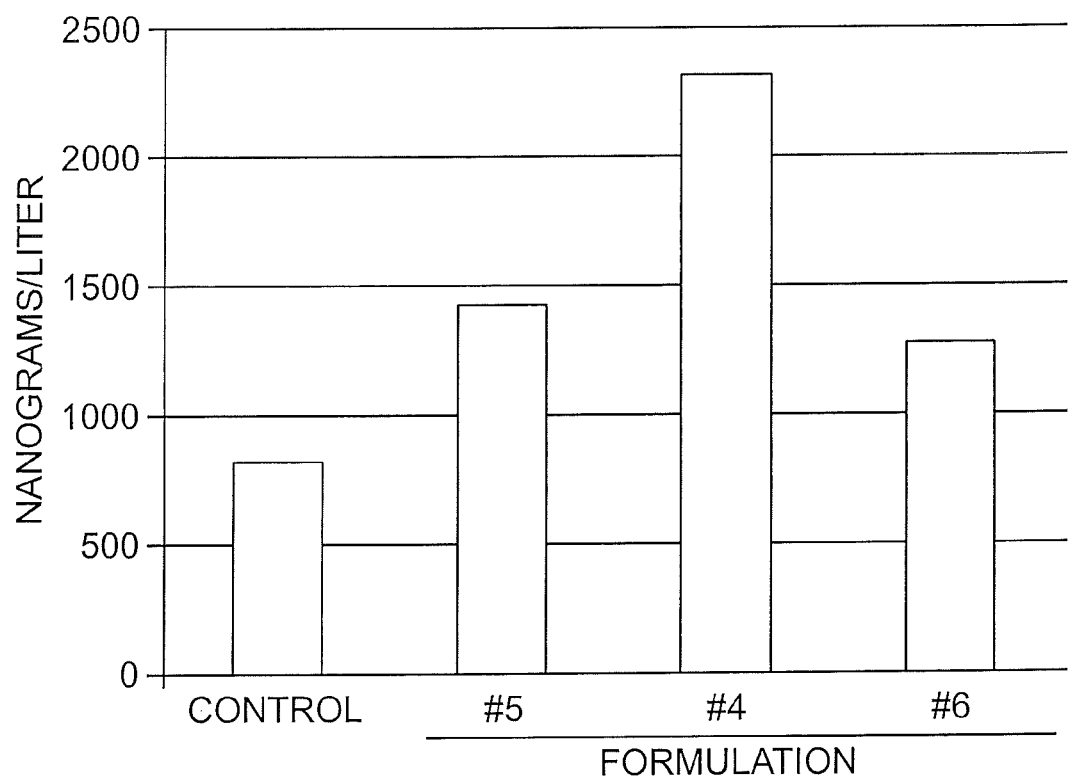
FIG. 2 shows the amount of fragrance measured over dry hair after treatment with base containing oil-continuous liquid crystalline phase formulations as compared to a control (neat fragrance equivalent).

In this example, the oil-surfactant mixture absorbed water upon introduction to the base to form the oil continuous lyotropic liquid crystal. As shown in FIG. 2, increased levels of fragrance in vapor above hair washed was achieved with products containing phases prepared with formulations #4-#6 compared to product with fragrance alone (incorporated normally with no surfactant phase).

Example 3: Cationic-Anionic Gemini Surfactant Systems

Figure 3:
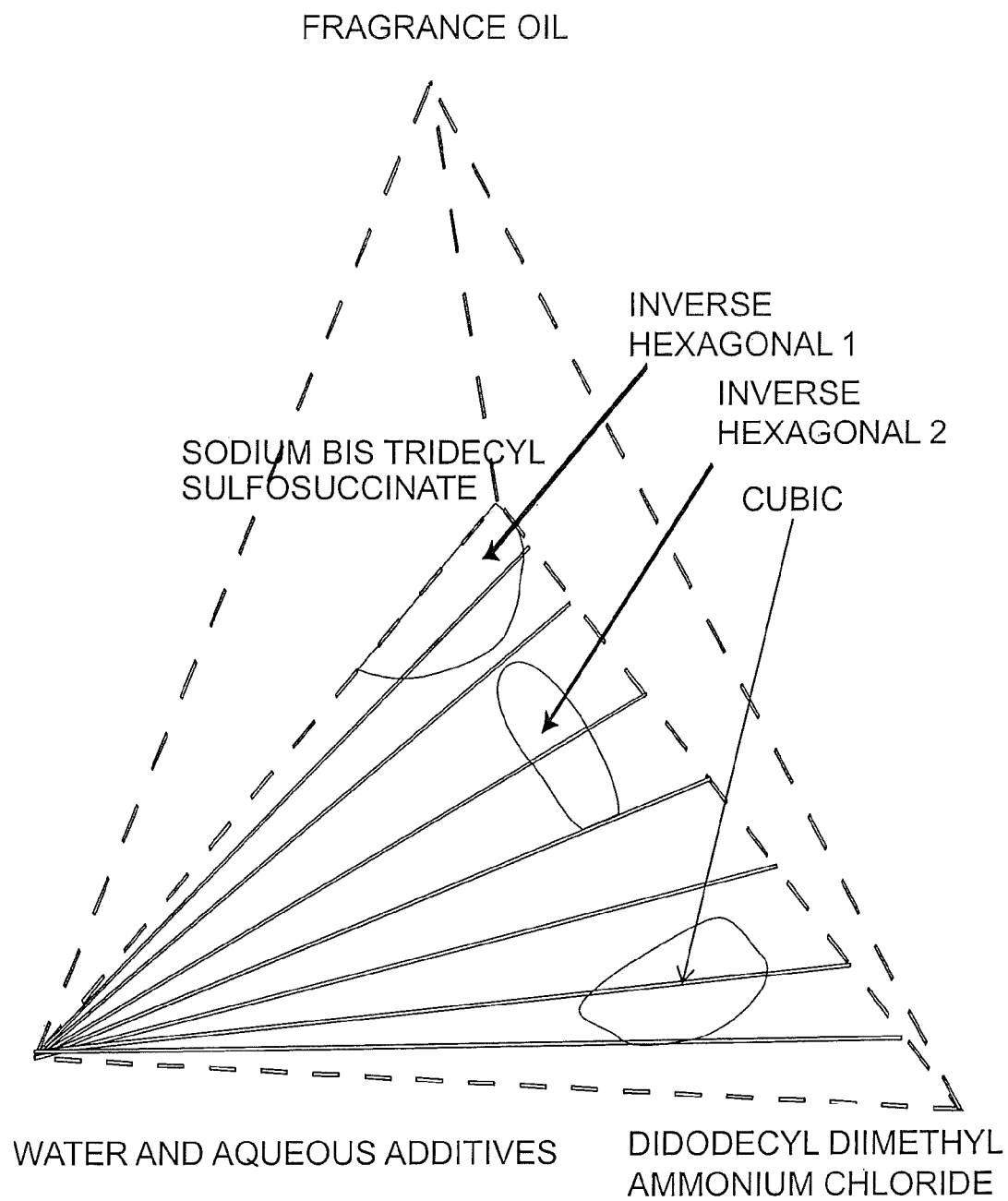
FIG. 3 shows three different oil continuous liquid crystal regions in a tridedcyl sulfosuccinate-diquat system.

The ratio of cationic to anionic surfactant is important to obtain the different liquid crystal phases (FIG. 3). However, the particular ratio is determined experimentally. In this respect, Table 3 provides representative examples of formulations that are based on different weight ratios of the same two surfactants.

TABLE 3

| Component | Inverse Hexagonal 1 | Inverse Hexagonal 2 | Cubic |
|---|---|---|---|
| Sodium Bis-Tridecyl Sulfosuccinate | 0.41 | 0.58 | 0.15 |
| Didodecyl Dimethyl Ammonium Chloride | 0.22 | 0.05 | 0.44 |

TABLE 3-continued

| Component | Inverse Hexagonal 1 | Inverse Hexagonal 2 | Cubic |
|---|---|---|---|
| Fragrance Oil | 0.28 | 0.28 | 0.26 |
| Water | 0.09 | 0.09 | 0.15 |

What is claimed is:

1. An oil-continuous liquid crystalline phase formulation consisting of sodium dioctyl sulfosuccinate, a cationic surfactant, and a fragrance oil.

2. The oil-continuous liquid crystalline phase formulation of claim 1, wherein the cationic surfactant comprises methyl bis(hydrogenated tallow amidoethyl)-2-hydroxyethyl ammonium methyl sulfate, methyl bis(tallow amidoethyl)-2-hydroxyethyl ammonium methyl sulfate, methyl bis(soya amidoethyl)-2-hydroxyethyl ammonium methyl sulfate, methyl bis(canola amidoethyl)-2-hydroxyethyl ammonium methyl sulfate, methyl bis(tallowamido ethyl)-2-tallow imidazolinium methyl sulfate, dioleoyl ammonium methosulfate, or didodecyl dimethyl ammonium chloride or dipalmityl ammonium methosulfate.

3. A method of preparing a consumer product comprising adding the oil-continuous liquid crystalline phase formulation of claim 1 to a consumer base.

* * * * *